June 28, 1949. S. WILMORE Plant Pat. 848

JUNIPER TREE

Filed Aug. 22, 1947

Inventor:
Scott Wilmore
By: Robert Cobb
Attorneys.

Patented June 28, 1949

Plant Pat. 848

UNITED STATES PATENT OFFICE

848

JUNIPER TREE

Scott Wilmore, Wheatridge, Colo.

Application August 22, 1947, Serial No. 770,068

1 Claim. (Cl. 47—59)

The present discovery relates to a new and distinct variety of ornamental juniper tree, a seedling cultivated in Jefferson County, Colorado, which from the color, leaf texture and growth habit I have determined belongs to the species *Juniperus scopulorum*, resembling more nearly in respect to the above characteristics the "Kenyon" variety. In its summer color it resembles the "Pathfinder" more than any other juniper, but is more silvery.

This new variety differs very much from any other juniper tree not only in its combination of characteristics, but primarily in respect to its silver-gray color and the fact that this color becomes more brilliant during the winter months when others become dull and drab. The more exposed to the winter sun, the more brilliant this tree color becomes, during this season.

Other equally desirable, advantageous, and novel characteristics are its slow growth habit and its natural pyramidal shape acquired without shearing. Its unusually heavy, and dense ascending foliage, even when the tree is young, combined with the brilliant aforementioned color, both in summer and winter, places this variety of Juniper in a position unknown commercially in respect to trees of this species up to now.

Asexual reproduction of this new variety shows the foregoing characteristics come true to form and are established.

Figure 1:
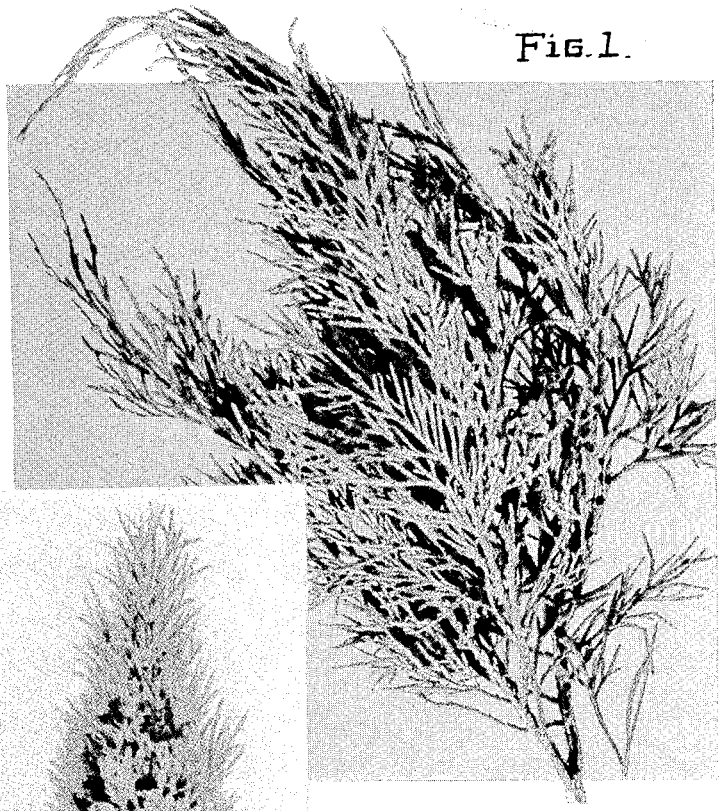
Figure 2:
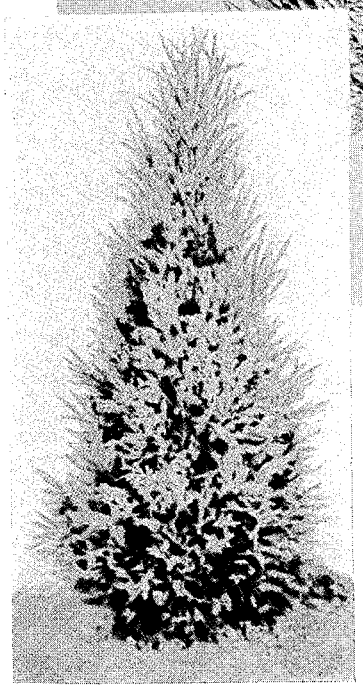

The accompanying drawing shows as nearly as possible to reproduce the color characteristic. In Fig. 1, is shown in detail a specimen branch of the tree, and in Fig. 2 an elevation of a fully developed tree specimen, particularly depicting the density of the foliage and the natural medium height growth and pyramidal shape of this variety.

The following is a more detail description of this new variety, color terminology being in accordance with Ridgway's Color Standard:

*Tree*

General characteristics: Medium height; vigorous; upright; pyramidal; dense, heavy whipcord foliage; slow growing; hardy.

*Colors.*—Ranging from the lightest, Glaucous Gray, Plate XLVIII, through Deep Glaucous Gray, Plate XLVIII, to Dark Medici Blue, Plate XLVIII.

Trunk: Slender; shaggy.

*Color.*—Rood's Brown, Plate XXVIII.

Branches: Ascending; stiff; snow resistant; with shreddy dull Cocoa Brown, Plate XXVIII, bark.

Branchlets: Extremely numerous; ascending; slender.

Leaves: Rhombic-ovate; acuminate; closely appressed; obscurely glandular.

*Color.*—Glaucous Gray, Plate XLVIII, with glaucous bloom.

Flowers: Staminate only; globose; small; obscure.

Use: Every type of landscaping.

Resistance to:

*Insects.*—Good.

*Disease.*—Good.

Shipping quality: Good.

I claim:

A new and distinct variety of Juniper tree, characterized as to novelty by its silver-gray color, and the habit of this coloring of growing more brilliant during the winter season, particularly increasing such brilliancy the more it is exposed to the sun; by the density of its whipcord foliage even in young growths; by its slow growing habit to average height; and by the natural pyramidal shape of the tree without shearing, substantially as shown and described.

SCOTT WILMORE.

No references cited.